United States Patent [19]

Bunn et al.

[11] Patent Number: 5,213,961
[45] Date of Patent: May 25, 1993

[54] ACCURATE QUANTITATION OF RNA AND DNA BY COMPETETITIVE POLYMERASE CHAIN REACTION

[75] Inventors: H. Franklin Bunn, Auburndale; Gary Gilliland, Wellesley; Kerry Blanchard, Brookline; Steven Perrin, Brighton, all of Mass.

[73] Assignee: Brigham and Women's Hospital, Boston, Mass.

[21] Appl. No.: 400,664

[22] Filed: Aug. 31, 1989

[51] Int. Cl.$^5$ .................. C12Q 1/68; C07H 17/00; C12P 19/34; C12N 15/00
[52] U.S. Cl. .................. 435/6; 435/91; 536/24.33; 536/24.3; 935/77; 935/78
[58] Field of Search .................. 435/6, 91; 536/27; 935/77, 78

[56] References Cited

U.S. PATENT DOCUMENTS 4,683,202 7/1987 Mullis .................. 435/91

FOREIGN PATENT DOCUMENTS 200362 12/1986 European Pat. Off. .
201184 12/1986 European Pat. Off. .
258017 3/1988 European Pat. Off. .

OTHER PUBLICATIONS

Chelly et al, Nature, 333 pp. 858-860 (1988).
Kwok et al, Nature, vol. 339, May 18, 1989, pp. 237-238.
Rappolee, D. A. et al., Science 241:708-712 (1988).
Chelly, J. et al., Nature 333:858-860 (1988).
Higuchi, R. et al., Nucl. Acids Res. 16(15):7351-7369 (1988).
G. Gilliland et al., UCLA Symposia on Molecular and Cellular Biology; The Polymerase Chain Reaction: Methodology and Applicatikons, Apr. 3-24, 1989, Keystone, Colo., pub'd in J. Cell Biochem., Supp 13E, p. 270 (1989).

Primary Examiner—Margaret Moskowitz
Assistant Examiner—Mindy B. Fleisher
Attorney, Agent, or Firm—Sterne, Kessler, Goldstein & Fox

[57] ABSTRACT

A process for quantitating nucleic acids species in a sample is described which comprises co-amplification of a competitive template with the sample template wherein the competitive template utilizes primers identical to those utilized by the sample template and wherein the competitive template is distinguishable from the sample template.

16 Claims, 3 Drawing Sheets

ACCURATE QUANTITATION OF RNA AND DNA BY COMPETETITIVE POLYMERASE CHAIN REACTION

STATEMENT AS TO RIGHTS TO INVENTIONS MADE UNDER FEDERALLY SPONSORED RESEARCH AND DEVELOPMENT

Part of the work leading to this invention utilized U.S. Government funds. The U.S. Government has certain rights in this invention.

FIELD OF THE INVENTION

The invention is in the field of molecular biology techniques. Specifically the invention is directed to methods of quantitating levels of specific RNA and DNA species by competitive polymerase chain reaction techniques.

BACKGROUND OF THE INVENTION

Further understanding of the regulation of gene expression depends in part on the ability to accurately measure levels of specific nucleic acid species (DNA and RNA) in defined cell populations. Recent advances in fluorescent cell sorting as well as cell culture technology provide access to homogeneous cell samples with well characterized maturational and/or developmental features.

However conventional methods of analysis of DNA and RNA, such as, for example, by Southern blot hybridization, Northern and "dot blot" hybridization, and even nuclease protection mapping, are not sensitive enough to detect levels of specific DNA or RNA species in many samples when such sample is limited by either low cell number or low copy number per cell. This problem is especially acute in samples of fluorescent cell-sorted populations and in samples of cultured cells. Moreover these methods permit only crude quantitation of the nucleic acid which is present.

In situ hybridization techniques do not solve this problem. In situ hybridization does allow detection of a specific DNA or RNA in single cells but is insensitive and non-quantitative.

Because of its extraordinary high sensitivity, the polymerase chain reaction (PCR) has proven useful in amplifying specific DNAs, including cDNAs, especially those present in low copy number or low abundance (Cohen, S. N., U.S. Pat. No. 4,293,652; Erlich, H. A. et al., EP 258,017; Mullis, K. B., EP 201,184; Mullis et al., EP 200,362; Saiki, R. K., et al., Science 239:487–491 (1988); Mullis, K. B. et al., Meth. Enzymol. 155:335–350 (1987); Scharf, R. K., et al., Science 233:1076–1079 (1986) and Saiki, R. K., et al., Science 230:1350–1354 (1985)).

The polymerase chain reaction amplifies a DNA sequence several orders of magnitude in a few hours. For example, it has been possible to amplify, subclone and characterize low abundance mRNA (Frohman, M. A., et al., Proc. Natl. Acad. Sci. 85:8998–9002 (1988)), and to detect unique mRNA transcripts from abnormal cells in a background of normal cells (Kawasaki, E. S., et al., Proc. Natl. Acad. Sci. 85:5698–5702 (1988), Lee, M-S., et al., Science 237:175–178 (1987)). The use of the polymerase chain reaction, as a DNA diagnostic technique has been recently reviewed (Ladegren, U., et al., Science 242:229–237 (1988)).

The polymerase chain reaction requires the use of oligonucleotide primers complementary to sequences flanking a particular region of interest for primer-directed DNA synthesis in opposite and overlapping directions. With repeated cycles of high-temperature template denaturation, oligonucleotide primer reannealing, and polymerasemediated extension, DNA sequences can be faithfully amplified several hundred-thousand fold.

Generally PCR requires knowledge of the sequence of both the 5' and the 3' end of the template being amplified so that two different primers for each template may be designed, one primer for the sense strand and one primer for the antisense strand. However, it is known in the art to amplify nucleic acid targets with only one primer, using "anchored PCR," wherein it is necessary only to know the sequence of the 3' end of the target. Loh, E. Y. et al., Science 243: 217 (1989).

In theory, only one copy of the target gene need be present in a sample for the polymerase chain reaction to adequately target and amplify it. For example, the polymerase chain reaction amplification technique has been used to analyze the DNA in an individual diploid cell and a single sperm. Li, H. et al., Nature 335: 414–417 (1988).

Although it has been possible to detect and amplify large amounts of rare DNA or mRNA transcripts, it has been more difficult to quantitate the amount of the nucleic acid species in the starting material for, although PCR can detect the presence of a targeted nucleic acid species in the starting material, the results of conventional PCR cannot be used to calculate the pre-amplification levels of that targeted nucleic acid. This has precluded the use of PCR in many situations, for example, in an analysis of the fold induction of a specific mRNA in response to exogenous stimuli.

The main constraint in obtaining quantitative data from conventional PCR is inherent in the amplification process. Because amplification is (at least initially) an exponential process, small differences in any of the variables which control reaction rate will dramatically affect the yield of PCR product. Variables which influence the rate of the PCR reaction include the concentrations of polymerase, deoxynucleoside triphosphate substrates (dNTP's), $Mg^{++}$, target DNA and primers; annealing, extension and denaturing temperatures; cycle length and cycle number; the rate at which the temperature is changed from one step to another within each amplification cycle; rate of "primer-dimer" formation; and presence of contaminating DNA.

Further, even when these parameters are controlled precisely, there is tube-to-tube variation which precludes accurate quantitation. For example, significant differences in yield occur in PCR samples which are prepared as a pool and then aliquoted into separate tubes and amplified in the same run. The basis for this variation is not certain—it may be related to events which occur during the first few cycles, or small temperature variances across the thermal cycler block.

Methods have been described for quantitating cDNA species by PCR, usually by co-amplifying a second, unrelated template (Rappolee, D. A., et al., Science 241:708–712 (1988)). These methods are critically dependent on several variables, including cycle number and amount of starting mRNA of each species. Even when these variables are adequately controlled, it is unlikely that the unrelated control template will be amplified at precisely the same rate as the unknown template. Small differences in the rate of amplification of the two templates are magnified during PCR and may grossly over- or underestimate the amount of the unknown template present.

For example, Chelly et al., Nature 333:858-860 (1988), attempt to overcome the above limitations of PCR in calculating pre-amplification levels of dystrophin mRNA by co-amplifying the target's mRNA with that of a reporter mRNA, aldolase A, and relating the fold amplification of the reporter molecule to that of the target. This method does give an approximation of the amount of a starting mRNA in the sample. However, Chelly et al.'s, method requires knowing primer sequences for two different targets and does not overcome differences in the rates of primer-dimer formation between the two sets of primers.

Although this approach has been successfully applied in several systems, data must be obtained at early cycle number (e.g. <20 cycles) when efficiency of amplification is a "constant". This often necessitates blotting of PCR products with labeled probe, with difficulties in quantitation inherent in blotting techniques, and is difficult to apply to low abundance mRNA from small numbers of cells.

Thus a need still exists for a method which adapts the sensitivity of PCR technology to quantitative analysis of the nucleic acid species being amplified.

SUMMARY OF THE INVENTION

Recognizing the role that PCR plays in molecular analysis of nucleic acid species, the inventors evaluated PCR technology in an effort to identify and overcome those factors which limit PCR's ability to be used as a quantitative technique. These efforts have culminated in the identification of a modification of standard PCR methods which is capable of providing quantitative information about the starting levels of the target being amplified. Specifically, the inventors have developed a modification of the PCR technique, herein termed competitive PCR, which provides for co-amplification of a standard's template concurrently with the target's template, wherein amplification of such standard's template is effected with the same primers used by the target, and wherein such standard's template can be distinguished from the target template following amplification in a detectable manner.

The inventors then successfully quantitated low levels of specific mRNA species by use of this PCR modification.

BRIEF DESCRIPTION OF THE DRAWINGS

FIGS. 3(A and B) Plot of the ratio of: GM-CSF gDNA/cDNA after amplification vs. gDNA added to the original mixture. FIG. 3A shows an expansion of the 0.1-1.0 ng range.

DEFINITIONS

In the description that follows, a number of terms used in molecular biology and PCR technology are extensively utilized. In order to provide a clearer and consistent understanding of the specification and claims, including the scope to be given such terms, the following definitions are provided.

"Complementary DNA" or a "cDNA" as used herein includes recombinant genes synthesized by reverse transcription of mRNA and from which intervening sequences (introns) have been removed.

"Template" as used herein refers to a nucleic acid polymer, such as DNA or RNA, which is capable of serving as a substrate for the enzymatic polymerization of a complementary nucleic acid strand. A "competitive" template as used herein, refers to a template which utilizes identical primers for PCR amplification as that of a "target" template but which differs from the target template in a manner which is detectable, for example, by a mutation, insertion or deletion of a portion of the sequence of the target template. As used herein, the "competitive" template is the standard's template and the "target" template is the template of the unknown whose levels it is desired to determine using the methods of the invention.

"Primer" as used herein refers to an oligonucleotide, preferably an oligodeoxynucleotide, which possesses a free 3'OH group which, upon hybridization to a nucleic acid template, is recessed relative to the 3' end of the template and thus is capable of acting as a site of initiation of the synthesis or polymerization of a nucleic acid polymer, the sequence of which is complementary to the template strand, in the presence of deoxynucleotide substrates, an appropriate enzyme capable of DNA replication, and a suitable temperature and pH. Primers that consist of the same sequence are said to be 100% homologous. Primers that are non-homologous consist of completely different sequences. Various degrees of intermediate homology are possible, for example, 50% homology, greater than 50%, and less than 50%.

It is not necessary that the primers used to prime synthesis of both strands of the standard's template be 100% homologous to the primers used to prime the respective strands of the target's template. It is necessary only that the primers be functionally equivalent in competitive PCR, that is, that the primers be of such a sequence that they prime amplification of the standard's and target's templates with an efficiency equivalent to that provided by using primers of the same sequence. Therefore, primers which are less than 100% homologous, and even completely non-homologous, would be useful in the methods of the invention if the primers are functionally equivalent. For the methods of the invention, primers are considered to be functionally equivalent, that is, functionally identical, if the results of competitive PCR analysis using such primers are quantitatively the same as the results of competitive PCR using 100% homologous primers for the standard and target.

In a similar manner, it is not necessary that the primer binding sites on both strands of the standard's template be 100% homologous to the primer binding sites on the respective strands of the target's template. It is necessary only that such primer binding sites be functionally identical such that they allow hybridization of functionally identical primers to the standard's and target's templates with an efficiency equivalent to that provided by using primer binding sites with 100% homology. For the methods of the invention, primer binding sites are considered to be functionally equivalent, that is, functionally identical, if the results of competitive PCR analysis using such primer binding sites are quantitatively the same as the results of competitive PCR using primer binding sites of 100% homology for both the standard and target.

The primers and primer binding sites of the standard and target may consist of different lengths as long as, as discussed above, the primers and primer binding sites are functionally equivalent.

Such functionally identical primers and primer binding sites may also be used with competitive anchored PCR.

"Amplification" as used herein refers to an increase in the amount of the pre-existing nucleic acid template.

DESCRIPTION OF THE PREFERRED EMBODIMENTS

The invention comprises methods for quantitating levels of specific nucleic acid species in samples utilizing a modification of PCR technology, herein termed "competitive PCR."

Specifically, the competitive PCR methods of the invention comprise concurrent PCR amplification (coamplification) of a standard's template with a target's template, wherein the PCR amplification of the standard's template utilizes primers identical to those utilized by the target and wherein the standard's template can be distinguished from that of the target in a detectable manner following amplification. The standard's template is added to the sample containing the target template in known amounts prior to the amplification such that by determining the fold amplification of the standard after PCR, the fold amplification of the target, and thus the initial, pre-amplification levels of the target, can be determined in a quantitative manner.

The competitive PCR methods of the invention obviate current problems which prevent accurate quantitation of starting levels of nucleic acids amplified by PCR.

Currently, the amount of amplified product produced by PCR amplification (X) can be estimated from the formula: $X\text{-}I(1+E)^n$, where I is the initial amount of target DNA, E is the average efficiency of a cycle of amplification and n is the number of cycles. The efficiency is not constant from cycle to cycle, and is determined by dependent and independent variables. E has a theoretic maximum value of 1, but declines during multiple cycles of amplification as a complex function related to consumption of primer, production of inhibitory pyrophosphates, and consumption of dNTPs, among other factors.

In the methods of the invention, rather than analyze a different reporter gene product, the template of the standard is a competitor DNA fragment which binds primers identical to those bound by the target of interest and which differs from the target of interest only by having either a small intron or a mutated internal restriction site. Therefore the same primers are used to coamplify the target and the competitor. The ratio of products remains precisely constant through the amplification. Following amplification, the relative amount of both the standard and target can be readily detected or visualized and measured by means well known in the art, for example, by ethidium bromide staining, biotin labelling or radiolabeling detection techniques.

In a preferred embodiment, the competitive template is a cDNA homologous to the target's sequence except that the competitive template has been altered, or mutated, such that it is now distinguishable from the target's template. For example, the competitive template may be mutated to contain a new restriction endonuclease site. The mutant template can then be distinguished from target cDNA by restriction enzyme digestion following PCR. Mutant templates suitable for use as standard templates in the methods of the invention are easily synthesized using PCR for site-directed mutagenesis by methods known to those of ordinary skill in the art, for example, by the method described in Higuchi, R., et al., *Nucl. Acids Res.* 16(15):7351–7369 (1988), incorporated herein by reference. Such mutation may be a deletion, insertion, or substitution anywhere along the length of the DNA fragment. A substitution suitable in the methods of the invention can be prepared in most cases by a single base pair change. Preferably, a single base pair change alters or creates a restriction enzyme site in the sequence and such site (or the lack thereof) may be used to distinguish the competitive template from the target template following amplification.

Alternatively, if the target is a cDNA which was synthesized from a mRNA, the target's genomic DNA or portions thereof can be used as the standard's competitive template, provided oligonucleotide primers are in separate exons and flank a small intron (100–200 bp). Such genomic DNA is most conveniently provided to the methods of the invention in the form of a plasmid. Amplified competitive (standard) template can then be distinguished from target cDNA by size. When genomic DNA is used, it is necessary that the size of an genomic intron (or introns) which is coamplified so as to distinguish the amplified product of the competitive standard from the target not be so large that the competitive DNA is not amplified as efficiently as target cDNA, either because of increased size, or increased duplex melting temperature.

In the methods of the invention, target cDNA is co-amplified with a dilution series of competitor DNAs of known concentration. Mutant template prepared as discussed above, to be used in the methods of the invention should be characterized by digestion with appropriate restriction enzymes and by accurate spectrophotometric ($A^{260}/A^{280}$) determination of concentration. A precise dilution series should be prepared ranging from 10 ng to 1 fg of template, in relatively large volumes (e.g., one ml) so that the same dilution series can be used for multiple concentration determinations.

Since a change in any of the variables listed above will affect yield of competitive template and target cDNA equally, relative ratios of the two should be preserved with amplification.

The relative amounts of target cDNA versus competitor can be measured following separation and detection of the amplified products, for example, by direct scanning of ethidium stained gels or by incorporation of radiolabeled dNTPs and autoradiography of the gel.

Preferably, after amplification, an aliquot of each sample is digested with an appropriate restriction enzyme and digested and undigested samples are run in parallel on a gel, for example a NuSieve/agarose gel. When amplification is performed using a genomic intron-containing competing template, samples may be run directly on gels and scanned or cut out for counting without restriction digestion.

For example, to quantitate the amount of PCR product, $^{32}$P-dCTP can be added to the competitive PCR reaction in a final concentration of 50 $\mu$Ci/ml. It is important not to adjust the concentration individual dNTP's in the dNTP stock (e.g. lowering the dCTP concentration to increase specific activity), as this will interfere substantially with amplification. Alternatively, a densitometer may be used to scan ethidium-stained gels to quantitate the amount of each PCR product present.

Because the starting concentration of the competitive template is known, the initial concentration of the target cDNA can be determined.

Competitive PCR can be used to accurately quantitate less than 1 pg of target cDNA from 1 ng of total mRNA, and can distinguish two-fold differences in mRNA concentration. The technique can be applied to quantitation of mRNA from as few as 10 cells, and is thus useful in screening cultured colonies of cells or flow-sorted cells for specific mRNA production under various conditions.

If the starting template is in the form of mRNA, it is necessary to reverse transcribe it into cDNA before performing competitive PCR. Adequate amounts of mRNA can be obtained from small numbers of cells by lysing in 0.5% NP-40, 10 mM Tris pH 8.0, 10 mM NaCl, 3 mM $MgCl_2$ for 5 minutes on ice, microfuging for 2 minutes to remove nuclei and cell debris, and performing reverse transcription on the supernatant fraction.

The technique is suitable for quantitation of DNA and RNA, and especially mRNA, tRNA and rRNA in eukaryotic or prokaryotic cells.

Primers for amplification by competitive PCR may be chosen with guidelines known to those in the art. Preferable primers are 20-40 mers and most preferably 30 mers, and are used with noncomplementary 3' ends, 50-60% GC content and minimal overlap with known sequences by analysis against the sequences contained in GenBank. However, primers of any size or sequence may be used if they bind to sites on the competitive template and target template so as to promote co amplification of such templates in a manner which preserves the quantitative relationship between the degree of amplification of the competitive template and the degree of amplification of the target template.

Primers are chosen to flank an intron so that amplified product is readily distinguished from contaminating genomic DNA that may be present. Preferably, primers are chosen which will give amplified fragments between 200-600 bp.

The dNTP stock which contains the deoxynucleotide substrates, dATP, dGTP, dCTP and dTTP, preferably contains a non-limiting amount of each deoxynucleoside triphosphate, for example, approximately 200-500 μM of each deoxynucleoside triphosphate. Concentrations of each deoxynucleoside triphosphate should be determined spectrophotometrically as described above before the addition of such substrate to the competitive PCR reaction of the invention.

The PCR is preferably performed is a buffered solution. For example, a buffer containing 50 mM KCl, 10 mM Tris-HCl, pH 8.3, 1.5 mM $MgCl_2$, and 0.01% w/v gelatin is useful in the methods of the invention. This buffer can conveniently be made and stored as a concentrated stock, for example, a 10× stock.

The competitive PCR methods of the invention can be performed with any polymerase capable of replicating the templates of the reaction in a nonlimiting manner. Preferably the Taq polymerase is used at a concentration which is nonlimiting for the reaction, for example, approximately 3-10 U/ml, and preferably 5 U/ml.

Accuracy is improved through use of master mixes which provide exactly the same amount of the various components to the different PCR tubes in the assay. For example, in one embodiment, a master mix is made which contains (per 90 μl): oligonucleotide primers (10-20 pmole each), dNTPs (200 μM in each as final concentration), 1.1× PCR buffer, Taq polymerase (0.5 U) and 10 μl of the RT mixture (following reverse transcription) as the source of the cDNA. Ninety μl of this mixture is added to 10 μl of previously prepared competitive template of known concentration in a dilution series.

Because quantitation of the results of competitive PCR amplification is not dependent on the variables noted above which affect quantitation of PCR amplifications, any conditions (annealing temperature, cycle length, cycle number, etc.) which give good amplification of template DNA can be used for quantitation by the competitive PCR methods of the invention.

When performing competitive PCR with a target whose concentration is completely unknown, it is desirable to conduct the quantitation in two separate competitive PCR steps. First, to obtain a rough estimate of the amount of DNA or cDNA present, a broad range of dilutions in log increments is used for a first competitive PCR titration. A second titration is then performed over a narrower (100 fold) range for precise quantitation.

Once the amount of target DNA or RNA in a sample is roughly known, in most cases, only the second series of titrations is necessary for a given set of experiments.

When using mutant templates containing altered restriction sites, heating to 94. for 4 minutes after completion of thermal cycling is desired to normalize for heteroduplex formation between mutant and wild-type strands.

The ratio of [competitive template/unknown template] plotted against competitive template is a hyperbolic relationship and approaches an asymptote when one species is present in vast excess. For this reason, most accurate results will be obtained when competitive template and unknown template are amplified at nearly equivalent concentrations. As noted above, performing an initial titration in log increments to determine the approximate concentration of the unknown cDNA is advised before performing a finer titration to obtain the most accurate results. Two-fold differences in cDNA concentrations can be accurately determined in this manner.

If the template being amplified is a RNA template, for example, an mRNA template, the template must first be transcribed into cDNA using an enzyme such as AMV or MLV reverse transcriptase. Several methods may be used to obtain mRNA suitable for reverse transcription. In general, highly purified mRNA gives best results for quantitation (e.g., guanidinium isothiocyanate lysis followed by centrifugation over $CsCl_2$ with at least two precipitation steps). It is not necessary to use poly-A purified mRNA. However, in many circumstances, it is desirable to use mRNA from very few cells, which effectively precludes standard techniques for mRNA purification. Adequate amounts of mRNA can be obtained from small numbers of cells by lysing in 0.5% NP-40 (Nonidet P-40), 10 mM Tris pH 8.0, 10 mM NaCl, 2 mM $MgCl_2$ for 5 minutes on ice, microfuging for 2 minutes to remove nuclei and cell debris, and performing reverse transcription on the supernatant fraction. Reverse transcription may be primed using an antisense primer which is specific for the gene of interest, or, with oligo dT, or random hexanucleotide primers. Oligo dT permits amplification of more than one gene from the same RT mixture, but the target sequence needs to be relatively close to the poly-A tail. Random hexanucleotide primers will prime all species of RNA present, and allow amplification of any desired target sequence from the RT mix.

Competitive PCR is capable of quantitating the amount of cDNA present in a given sample, but if the efficiency of the reverse transcription of mRNA into cDNA is less than 100%, the method will underestimate the actual amount of mRNA present. In order to obtain an internal mRNA control, random hexanucleotides may be used to prime the RT reaction, using competitive PCR to assay the amount of cDNA of a "housekeeping" gene, such as $\beta$-actin. Alternatively, a known amount of mutant cRNA template prepared by use of T7 polymerase can be added to the RT mixture as an internal standard.

The advantages of this technique are that: a) quantitation is independent of the many variables which affect the PCR reaction, and b) it is more sensitive than Northern blotting or ribonuclease protection assays for specific mRNAs. For example, the technique may be readily applied to screening colonies of cells for specific mRNA.

Competitive PCR lends itself to a broad array of useful applications. Because it can accurately measure mRNA species in a small number of cells (less than 100), this strategy can be used to analyze gene expression in cells isolated by fluorescent sorting or cells plucked from colonies grown in semi-solid medium. Because competitive PCR enables quantitative determination of low abundance mRNAs, low level (constitutive) expression of genes can be characterized.

The sensitivity and specificity of this method also lends itself to the quantitation of mRNAs expressed by reporter genes such as human growth hormone used in transfection experiments to evaluate putative regulatory sequences. Competitive PCR allows quantitation of mRNA from reporter genes directly, bypassing the need for translation, secretion, and detection of a protein product from a transfected cell line. It should also allow for selection of colonies of transfected cells which produce unusually high or low levels of mRNA. Indeed, by means of an appropriate mutation within the region that is amplified, the gene under study can serve as its own reporter. As described above the endogenous mRNA can be directly compared to the exogenous mRNA by digestion of the amplified products with the appropriate restriction enzyme. This approach should permit study of regulatory elements of a gene in the most "native" possible context.

Competitive PCR is also useful in the detection and quantitation of low abundance species of DNA such as somatic cell mutations and integration of viral DNA, both of which may involve only a small minority of a given cell population. Efficiency of transfection of plasmids can also be accurately monitored. Finally, this approach can be applied to measurements of gene dosage, both gene amplification and deletion. There are a number of useful applications of quantitative competitive PCR for estimating gene dosage, including: a) analysis of somatic cell mutations; b) monitoring the efficiency of transiently transfected cells; and c) determining the copy number of genes introduced into cells, stably transfected either with plasmids or with retroviral vectors.

Having now generally described this invention, the same will be better understood by reference to certain examples which are included herein for purposes of illustration only and are not intended to be limiting unless otherwise specified.

EXAMPLES

EXAMPLE 1

Reverse Transcription of mRNA Templates
Preparation of GM-CSF cDNA (cGM)

Reverse transcription was performed in a 20 $\mu$l assay mixture containing:
a. about 10 ng of total MLA-144 cell RNA, (the supernatant fraction prepared by lysing approximately $10^7$ MLA-144 cells in 0.5% NP-40, 10 mM Tris pH 8.0, 10 mM NaCl, and 3 mM $MgCl_2$ for 5 minutes on ice, and then microfuging for 2 minutes to remove nuclei and cell debris). This is the source of the GM-CSF mRNA to be reverse transcribed;
b. Reverse transcription primer (20-50 pmoles of oligo dT);
c. dNTP (500 $\mu$M in each nucleotide);
d. 1× PCR buffer;
e. 1.0 Unit of reverse transcriptase;
f. dithiothreitol, 1 mM final concentration;
g. RNAse inhibitor, 2-5 units; and
h. diethylpyrocarbonate treated water Reverse transcription was effected by incubating the above mixture at 37° for one hour.

EXAMPLE 2

Competitive PCR Amplification of GM-CSF cDNA (cGM)

To demonstrate the quantitative power of competitive PCR, a plasmid containing the full-length cGM sequence was used as a "target" template. A known amount of the target template was added and the ability of competitive PCR to confirm this value was investigated as below.

A master mix was prepared which contained:
a. GM-CSF sense primer (30 mer, 5 nmol/ml), 48 $\mu$l;
b. GM-CSF antisense primer, (30 mer, 5 nmol/ml), 48 $\mu$l;
c. dNTP stock (2.5 mM in each), 96 $\mu$l;
d. cGM cDNA (known concentration of 0.6 ng/$\mu$l), 12 $\mu$l;
e. 10× PCR buffer, 120 $\mu$l;
f. Water, 756 $\mu$l; and
g. Taq polymerase (5.0 units/$\mu$l), 1.2 $\mu$l.

Figure 1:
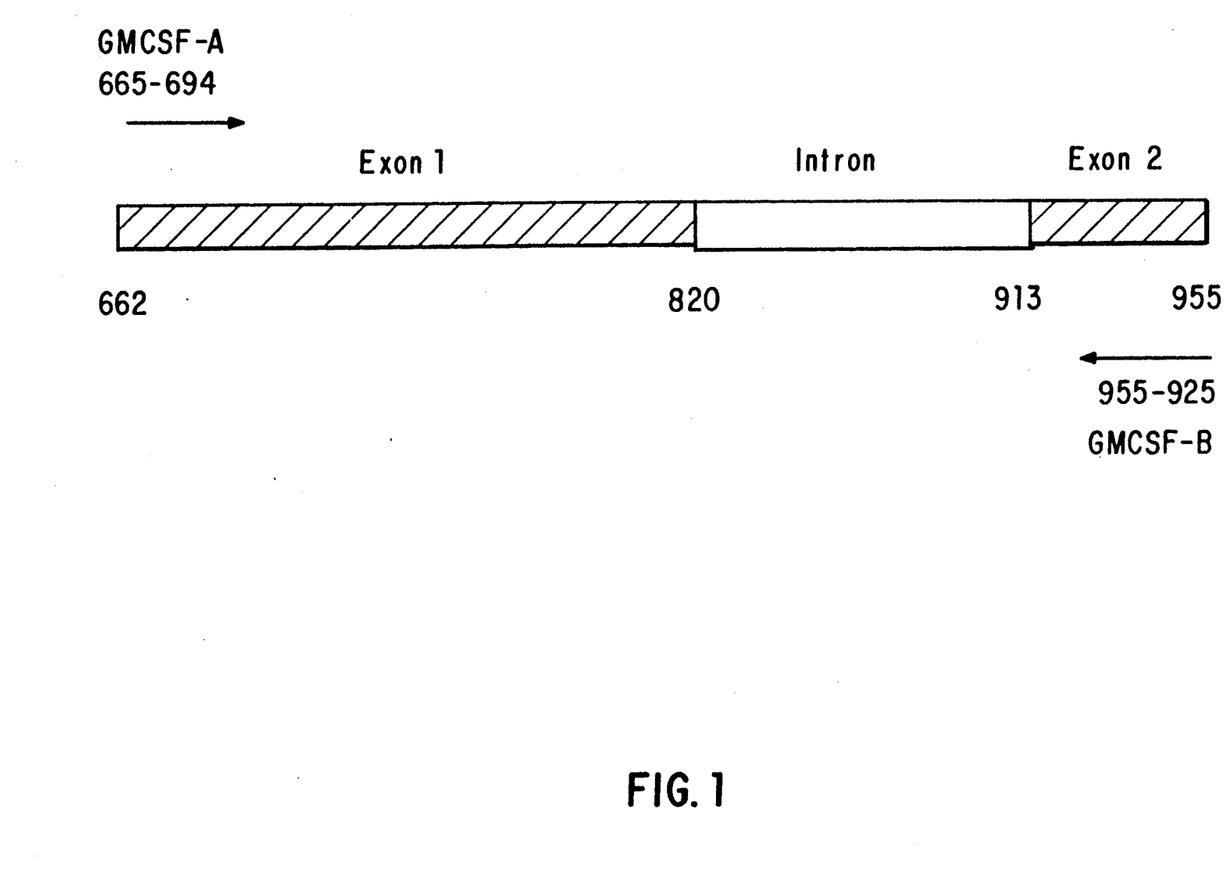
FIG. 1. Granulocyte-Macrophage Colony Stimulating Factor (GM-CSF) genomic map. Positions of the oligonucleotide primers are noted as GMCSF-A (665-694) and GMCSF-B (925-955). The amplified genomic DNA is 290 bp. The amplified cDNA is 197 bp.

The standard template was the genomic GM-CSF (gGM) shown in FIG. 1. Primers were chosen from exon 1 and exon 2 to give a 197 bp fragment when cDNA is amplified and a 290 bp fragment when genomic DNA is amplified (FIG. 1).

A series of assay samples were set up containing varying amounts of the standard's competitive GM-CSF gDNA template as follows:

| Tube | gGM (competitive template) |
|---|---|
| 1 | 10.0 ng/$\mu$l, 10 $\mu$l; |
| 2 | 1.0 ng/$\mu$l, 10 $\mu$l; |
| 3 | 0.8 ng/$\mu$l, 10 $\mu$l; |

| Tube | gGM (competitive template) |
| --- | --- |
| 4 | 0.6 ng/µl, 10 µl; |
| 5 | 0.4 ng/µl, 10 µl; |
| 6 | 0.2 ng/µl, 10 µl; |
| 7 | 0.1 ng/µl, 10 µl; |
| 8 | 0.08 ng/µl, 10 µl; |
| 9 | 0.06 ng/µl, 10 µl; |
| 10 | 0.04 ng/µl, 10 µl; |
| 11 | 0.02 ng/µl, 10 µl; |
| 12 | 0.01 ng/µl, 10 µl; and |
| 13 | 0.001 ng/µl, 10 µl. |

For the competitive PCR assay, 90 µl of master mix was added to the 10 µl of each standard dilution tube shown above and competitive PCR was performed for 40 "cycles," with each cycle consisting of incubation at 94° for 1 min, 62° for 1 min, and 72° for 2 min.

Following competitive PCR amplification, gel electrophoresis was performed to analyze the results by electrophoresing 20 µl/well in triplicate on a 2.5% Nusieve/1% Agarose gel containing ethidium bromide. The intensity of the bands was quantitated by densiometric analysis.

Figure 2:
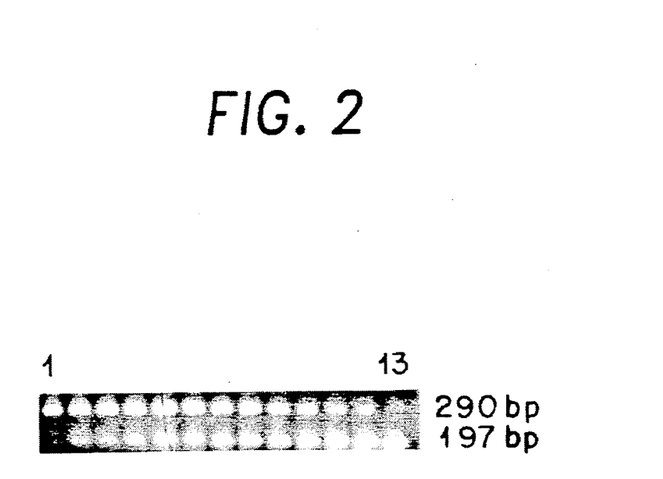
FIG. 2. Amplification of GM-CSF genomic DNA (gDNA) vs. cDNA. Lanes 1-13 contain varying amounts of GM-CSF gDNA competed against a fixed concentration of GM-CSF cDNA (0.6 ng) Lane 1, 100 ng; lane 2, 10.0 ng; lane 3, 8.0 ng; lane 4, 6.0 ng; lane 5, 4.0 ng; lane 6, 2.0 ng; lane 7, 1.0 ng; lane 8, 0.80 ng; lane 9, 0.60 ng; lane 10, 0.40 ng; lane 11, 0.20 ng; lane 12, 0.10 ng; and lane 13, 0.01 ng.
Figure 3A:
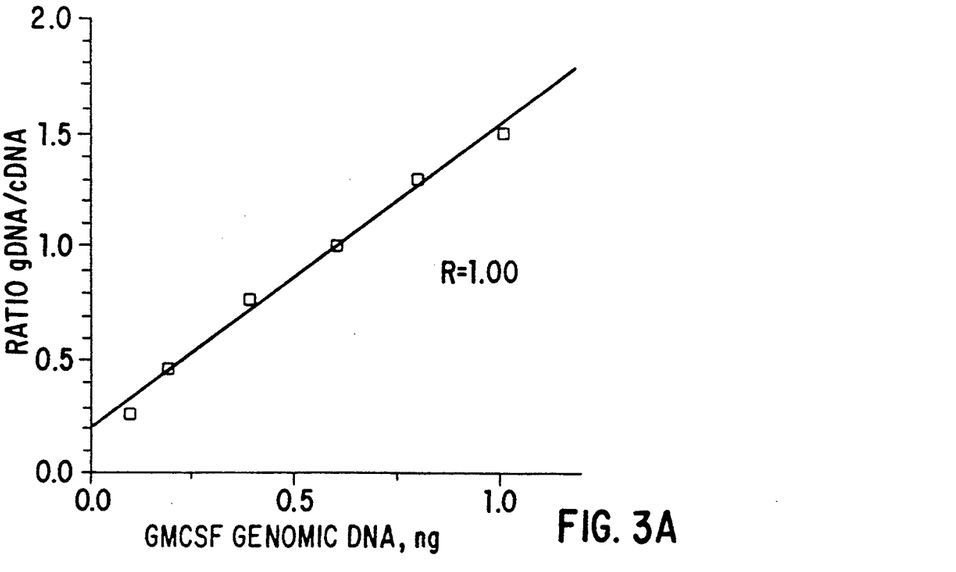
Figure 3B:
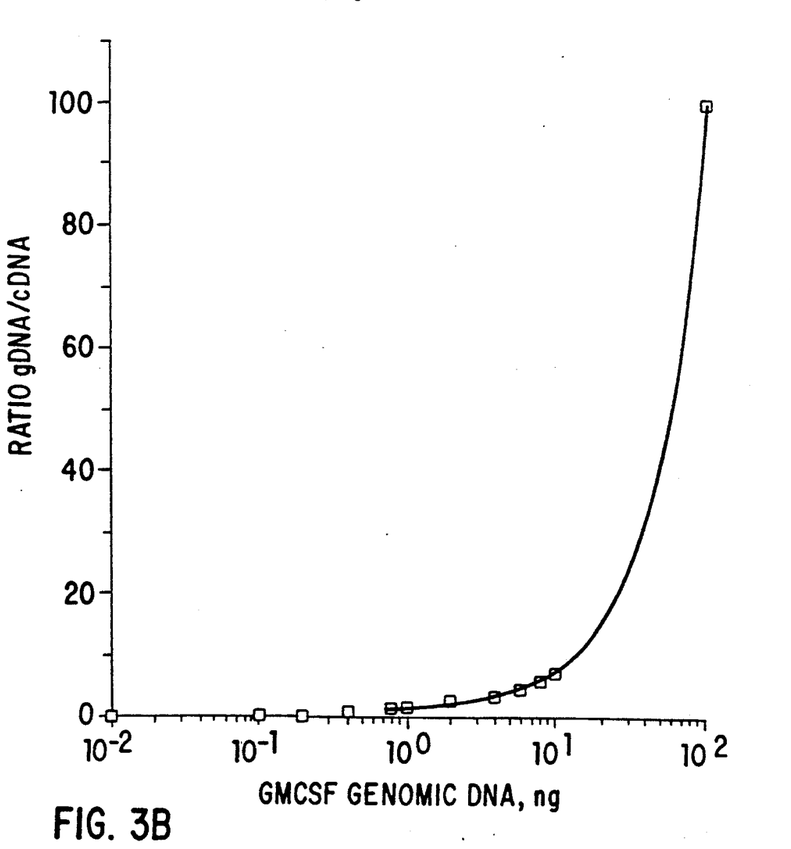

FIGS. 2-3 demonstrate quantitation of cGM levels in the samples amplified as above. The amount of gGM and cGM present in each lane was determined as follows. The photographed gel was analyzed by densitometry (FIG. 2). If bands contain $^{32}$P-dCTP, the labeled bands can be cut out and counted. The amount of gGM determined by the densiometric analysis is multiplied by the ratio of cGM bp/gGM bp to correct for increased label/ethidium staining per mole by the larger fragment. gGM/cGM can then be plotted as a function of the amount of known competitive gGM (FIG. 3). The point of equivalence (i.e., where there is a 1:1 ratio) is where cGM=gGM and represents the concentration of cDNA in the unknown. As shown in FIG. 3, competitive PCR determined that there were 0.62 ng of the target template in the sample, in excellent agreement with the added amount.

EXAMPLE 3

Analysis of Gene Dosage by Quantitative Competitive PCR

The example outlined briefly below describes an accurate estimation of gene dosage utilizing human-hamster hybrid cell lines containing specific human chromosomes. The results of this protocol provide a rigorous analysis of the sensitivity and range of competitive PCR for measuring gene dosage.

Human hamster heterokaryons were prepared by fusing dihydrofolate reductase (DHFR)-deficient Chinese hamster ovary cells with human bone marrow cells from a patient with a 5Q− syndrome, by means of polyethylene glycol. The hybrid cells were selected for retention of human chromosome 5 by growing colonies in selective media which permit growth of cells which have acquired human DHFR localized near the centromere in human chromosome 5.

Colonies were grown in selective media and analyzed by standard cytogenetic analysis as well as by chromosome 5 specific enzymes for the presence of human chromosome 5. Approximately half of the hybrid cell lines contained the normal homologue (5Q+), whereas the other half contained the 5Q− homologue, which has an interstitial deletion (5Q11-32). Among the genes included in this large deletion are those encoding granulocyte macrophage colony-stimulating factor (GM-CSF), as well as interleukin-3 (IL-3).

To quantitate gene dosage, mixtures of 5Q+ cells and 5Q− cells were analyzed using GM-CSF and IL-3 cDNAs as competitors. Primers which spanned short introns were used as above. The amplified product from genomic DNA was distinguished from the competitive cDNA by a difference in the size of the amplified fragment.

As a control, a unique (single copy) portion of the human DHFR gene was analyzed by competitive PCR.

Serial two-fold dilutions of competitor were added to the PCR reaction solutions containing genomic DNA from the 5Q+ and 5Q− mixtures described above.

Titrations, as described previously for analysis of cDNAs, establish the fraction of 5Q+ in the cell mixtures and interpretation of the results as described in the previous example allowed calculation of the gene dosage.

Now having fully described this invention, it will be understood by those with skill in the art that the scope may be performed within a wide and equivalent range of conditions, parameters, and the like, without affecting the spirit or scope of the invention or of any embodiment thereof.

What is claimed is:

1. A method for determining the amount of a target nucleic acid sequence in a sample, said method comprising (a) co-amplification of a target nucleic acid sequence and a known amount of a standard nucleic acid sequence in the same assay sample, wherein said target nucleic acid sequence and said standard nucleic acid sequence bind primers consisting essentially of the same sequence during said co-amplification and wherein said standard nucleic acid sequence differs from said target nucleic acid sequence such that either a restriction enzyme recognition site is created or destroyed, or sufficient contiguous bases are added to or deleted from said target nucleic acid sequence such that the size difference between said target nucleic acid sequence and said standard nucleic acid sequence can be detected by gel electrophoresis;

(b) detecting products of said co-amplification using gel electrophoresis; and (c) determining the amount of said target nucleic acid sequence in said sample.

2. A method for determining the amount of a target nucleic acid sequence in a sample, said method comprising:

(a) adding a known amount of a standard nucleic acid sequence to a sample that contains said target nucleic acid sequence, wherein said standard nucleic acid sequence and said target nucleic acid sequence bind amplification primers consisting essentially of the same sequence, and wherein said standard nucleic acid sequence differs from said target nucleic acid sequence such that either a restriction enzyme recognition site is either created or destroyed or sufficient contiguous bases are added to or deleted from said target nucleic acid sequence such that the size difference between said target nucleic acid sequence and said standard nucleic acid sequence can be detected by gel electrophoresis;

(b) adding said amplification primers to said sample;

(c) co-amplifying said target nucleic acid sequence and said standard nucleic acid sequence under conditions wherein said standard nucleic acid sequence and said target acid sequence bind said amplification primers;

(d) detecting products of said co-amplifications using gel electrophoresis; and (e) determining the amount of said target nucleic acid sequence in said sample from the amount of amplification of said standard nucleic acid sequence.

3. The method of any one of claims 1 or 2, wherein said nucleic acid sequence is DNA.

4. The method of any one of claims 1 or 2, wherein said nucleic acid sequence is RNA.

5. The method of claim 4, wherein said RNA is mRNA.

6. The method of any one of claims 1 or 2, wherein said amplification primers consist of the same sequence.

7. The method of any one of claims 1 or 2, wherein said standard nucleic acid sequence comprises a genomic sequence of said target template.

8. The method of any one of claims 1 or 2, wherein said standard nucleic acid sequence is a mutation of said target template.

9. The method of claim 8, wherein said mutation is the addition of a restriction enzyme site.

10. The method of claim 8, wherein said mutation is the removal of a restriction enzyme site.

11. The method of claim 8, wherein said mutation is the addition of an intron sequence.

12. The method of claim 11, wherein said intron is 100–200 bp.

13. The method of claim 8, wherein said mutation is the removal of an intron sequence.

14. The method of any one of claim 1 or 2, wherein said primer is a 20–40 mer.

15. The method of any one of claims 1 or 2, wherein said primer contains 50–60% GC content.

16. The method of any one of claims 1 or 2, wherein the amplification of said nucleic acid sequences result in an amplified product of 200–266 bp.

* * * * *